(12) United States Patent
Eberhardt et al.

(10) Patent No.: US 8,017,808 B2
(45) Date of Patent: Sep. 13, 2011

(54) PROCESS FOR PREPARING AN AMINE

(75) Inventors: Jan Eberhardt, Mannheim (DE); Bram Willem Hoffer, Heidelberg (DE); Frank Haese, Dietzenbach (DE); Johann-Peter Melder, Böhl-Iggelheim (DE); Bernd Stein, Alsbach-Hähnlein (DE); Michael Stang, Ludwigshafen (DE); Thomas Hill, Ludwigshafen (DE); Ekkehard Schwab, Neustadt (DE)

(73) Assignee: BASF SE, Ludwigshafen (DE)

( * ) Notice: Subject to any disclaimer, the term of this patent is extended or adjusted under 35 U.S.C. 154(b) by 375 days.

(21) Appl. No.: 12/293,609

(22) PCT Filed: Mar. 13, 2007

(86) PCT No.: PCT/EP2007/052332
§ 371 (c)(1),
(2), (4) Date: Sep. 19, 2008

(87) PCT Pub. No.: WO2007/107477
PCT Pub. Date: Sep. 27, 2007

(65) Prior Publication Data
US 2009/0082562 A1  Mar. 26, 2009

(30) Foreign Application Priority Data
Mar. 21, 2006 (EP) .................................. 06111505

(51) Int. Cl.
*C07C 209/16* (2006.01)
(52) U.S. Cl. ..................................................... 564/480
(58) Field of Classification Search .................. 564/480
See application file for complete search history.

(56) References Cited

U.S. PATENT DOCUMENTS

| | | |
|---|---|---|
| 3,275,554 A | 9/1966 | Wagenaar |
| 3,751,475 A | 8/1973 | van der Voort et al. |
| 4,521,624 A | 6/1985 | Jackisch |
| 4,832,702 A | 5/1989 | Kummer et al. |
| 6,437,206 B1 | 8/2002 | Meyer et al. |
| 6,821,396 B2 | 11/2004 | Wolfert et al. |
| 6,986,833 B2 | 1/2006 | Wölfert et al. |
| 7,105,662 B2 | 9/2006 | Henningsen et al. |
| 7,750,189 B2 * | 7/2010 | Kubanek et al. .............. 564/480 |
| 2008/0200727 A1 | 8/2008 | Eberhardt et al. |

FOREIGN PATENT DOCUMENTS

| | | |
|---|---|---|
| CA | 1122981 A | 5/1982 |
| CA | 2583155 A1 | 4/2006 |
| DE | 1179947 | 10/1964 |
| DE | 2125039 | 12/1971 |
| DE | 2118283 | 11/1972 |
| DE | 3611230 A1 | 10/1987 |
| DE | 19734975 A1 | 3/1999 |
| DE | 102005019540 A1 | 11/2006 |
| EP | 0007093 A1 | 1/1980 |
| EP | 0312253 A2 | 4/1989 |
| EP | 0611137 A1 | 8/1994 |
| EP | 0992284 A2 | 4/2000 |
| EP | 1312599 A1 | 5/2003 |
| EP | 1312600 A1 | 5/2003 |
| GB | 1396985 | 6/1975 |
| WO | WO-02/074755 A1 | 9/2002 |
| WO | WO-2006/040159 A1 | 4/2006 |

* cited by examiner

*Primary Examiner* — Rei-tsang Shiao
(74) *Attorney, Agent, or Firm* — Connolly Bove Lodge & Hutz LLP

(57) ABSTRACT

A process for preparing an amine by reacting an aldehyde and/or ketone with hydrogen and a nitrogen compound selected from the group of primary and secondary amines in the presence of a heterogeneous catalyst, wherein the catalyst is a coated catalyst which comprises at least one metal of group VIII of the Periodic Table of the Elements as a hydrogenating metal and additionally a promoter on an oxidic support, at least 80% of the metal of group VIII of the Periodic Table of the Elements being present in a layer between the surface of the catalyst and a penetration depth which is not more than 80% of the radius of the catalyst, calculated from the surface of the catalyst.

27 Claims, No Drawings

PROCESS FOR PREPARING AN AMINE

RELATED APPLICATIONS

This application is a national stage application (under 35 U.S.C. §371) of PCT/EP2007/052332, filed Mar. 13, 2007, which claims benefit of European Application No. 06111505.1, filed Mar. 21, 2006.

The present invention relates to a process for preparing an amine by reacting an aldehyde and/or ketone with hydrogen and a nitrogen compound selected from the group of primary and secondary amines in the presence of a heterogeneous catalyst.

The process products find use, inter alia, as intermediates in the preparation of fuel additives (U.S. Pat. No. 3,275,554; DE-A-21 25 039 and DE-A-36 11 230), surfactants, medicaments and crop protectants, hardeners for epoxy resins, catalysts for polyurethanes, intermediates for preparing quaternary ammonium compounds, plasticizers, corrosion inhibitors, synthetic resins, ion exchangers, textile assistants, dyes, vulcanization accelerants and/or emulsifiers.

For the preparation of an amine by reacting an aldehyde or ketone with hydrogen and a nitrogen compound, for example, high-pressure processes are known. Here, the hydrogenating amination is effected over a fixed catalyst bed, for which, for example, metal catalysts comprising Ni, Pd, Pt, promoters on a support are used.

DE-A-211 82 83 (BASF AG) relates to a process for preparing secondary or tertiary aliphatic or cycloaliphatic amines using a Pd/Ag catalyst which is not a coated catalyst. The support material is in particular $SiO_2$.

EP-A1-7093 (BASF AG) relates to the preparation of N-aralkyl-2,6-dimethylmorpholines, for example fenpropimorph, over Pd/Ag catalysts which are not coated catalysts. The support material is in particular $SiO_2$.

WO-A1-2002 074755 (=EP-A-1 373 232) (BASF AG) describes the preparation of 2,6-dialkylmorpholines, for example dodemorph, over catalysts whose active component consists essentially of platinum group metals. A particularly preferred support is $ZrO_2$.

German patent application No. 102005019540.7 of Apr. 27, 2005 (BASF AG) relates to a process for preparing an amine by reacting an aldehyde and/or ketone with hydrogen and a nitrogen compound selected from the group of primary and secondary amines, in the presence of a heterogeneous catalyst, the catalyst being a catalyst packing which can be prepared by applying at least one catalytically active metal and/or at least one compound of this metal to a fabric, a knit or a foil as a support material.

For the preparation of an amine by hydrogenating amination, low-pressure processes are also known. For example, noble metal catalysts in suspension mode are used, as described in U.S. Pat. No. 4,521,624 (Ethyl Corp.) for the preparation of, in particular, N,N-dimethylcyclohexylamine (DMCHA) over Pd/C.

EP-A1-611 137 (Sumitomo Chem. Comp.) relates to the reductive amination of cyclic ketones, a corresponding imino compound being prepared in a first stage and then hydrogenated.

EP-A2-312 253 (Kao Corp.) describes the use of specific copper catalysts in the preparation of N-substituted amines from alcohols or aldehydes.

It is an object of the present invention, while overcoming one or more disadvantages of the prior art, to discover an improved economically viable process for preparing an amine. In particular, the process should include a catalyst of high activity, which exhibits particularly high selectivity in the reaction.

Accordingly, a process has been found for preparing an amine by reacting an aldehyde and/or ketone with hydrogen and a nitrogen compound selected from the group of primary and secondary amines in the presence of a heterogeneous catalyst, wherein the catalyst is a coated catalyst which comprises at least one metal of group VIII of the Periodic Table of the Elements as a hydrogenating metal and additionally a promoter on an oxidic support, at least 80% of the metal of group VIII of the Periodic Table of the Elements being present in a layer between the surface of the catalyst and a penetration depth which is not more than 80% of the radius of the catalyst, calculated from the surface of the catalyst.

The metal of group VIII of the Periodic Table of the Elements is preferably present essentially in homogeneous distribution in the defined shell.

The promoter is preferably present in essentially homogeneous distribution over the entire cross section of the catalyst.

The advantages of the process according to the invention include good chemical activity of the catalyst, the high mechanical stability of the catalyst support and the very good selectivity of the catalyst. In particular, the overhydrogenation of the starting material (ketone or aldehyde) to the corresponding alcohol is observed only to a very small degree. In the synthesis, feedstock cost advantages consequently arise. The process according to the invention can also produce active ingredients with defined stereochemistry in a particularly advantageous manner, since the stereochemical information is preserved in the course of the synthesis with high selectivity. Side reactions, such as the unselective transfer of substituents, are also observed only to a slight degree, if at all, in the synthesis of unsymmetrically substituted amines. The high activity of the catalyst used in accordance with the invention further enables the performance of the reaction at reduced pressure and/or reduced temperature, which additionally increases the selectivity of the reaction. The possibility of being able to perform the reductive amination at lower pressure, for example 90 bar instead of 140 bar, with nevertheless very high space-time yields enables the commissioning of production plants with significantly lower capital costs (lower pressure level).

The catalyst used in the process according to the invention is characterized as follows and can be prepared as follows. The preparation is also described in the prior BASF patent application PCT/EP2005/011026 of Oct. 13, 2005.

In the catalyst used in accordance with the invention, at least 80% of the metal of group VIII of the Periodic Table of the Elements is present in a layer between the surface of the catalyst and a penetration depth which is not more than 80% of the radius of the catalyst, calculated from the surface of the catalyst.

In a preferred embodiment, the catalyst used has a diameter of from 1.5 to 10 mm, at least 80% of the metal of group VIII of the Periodic Table of the Elements being present in a layer between the surface of the catalyst and a penetration depth of not more than 1000 µm, calculated from the surface of the catalyst.

The metal of group VIII of the Periodic Table of the Elements is preferably present essentially in homogeneous distribution in the defined shell.

The promoter is preferably present in essentially homogeneous distribution over the entire cross section of the catalyst.

The invention thus provides a catalyst in which the metal of group VIII of the Periodic Table of the Elements forms a coating structure in the catalyst.

The groups of the Periodic Table of the Elements are designated in accordance with the CAS (Chemical Abstracts Service) nomenclature.

The catalyst used in accordance with the invention preferably has a diameter in the range from 1.5 to 9 mm. In particularly preferred embodiments, the diameter of the catalysts used in accordance with the invention is from 2.0 to 5 mm, in particular from 2.5 to 3.5 mm.

In the catalyst used in accordance with the invention, preferably at least 80%, preferably at least 90%, more preferably at least 95%, in particular at least 98%, especially 100%, of the metal of group VIII of the Periodic Table of the Elements is present in a layer between the surface of the catalyst and a penetration depth of not more than 1000 µm, calculated from the surface of the catalyst.

The catalyst used in accordance with the invention comprises a metal of group VIII of the Periodic Table of the Elements (Fe, Ru, Os, Co, Rh, Ir, Ni, Pd, Pt). In a preferred embodiment of the present invention, it is palladium.

The catalyst used in accordance with the invention additionally comprises at least one promoter. For example, it may comprise further metals of group VIII, IB and IIB of the Periodic Table of the Elements (Cu, Ag, Au, Zn, Cd, Hg). In a preferred embodiment, the catalysts used in accordance with the invention comprise, in addition to the metal of group VIII of the Periodic Table of the Elements, also at least one metal from group IB of the Periodic Table of the Elements. Particular preference is given here to silver.

In a particularly preferred embodiment, the catalyst used in accordance with the invention comprises palladium and silver.

The catalyst used in accordance with the invention may have any shapes, for example extrudates, hollow extrudates, tablets, rings, spherical particles or spheres. It is preferred when the catalyst is in the form of an extrudate.

The metals may be present in pure metallic form, but also in the form of compounds, for example in the form of metal oxides. Under the operating conditions of the amination process, they are generally present in the form of metals. The conversion of any oxides to metals can be effected in the manner known to those skilled in the art before the catalyst is used in a hydrogenation process within or outside a hydrogenation reactor, for example by prereduction and, if required or advantageous for manipulations with the prereduced catalyst, subsequent surface passivation.

The content in the catalyst of metal or metals of group VIII of the Periodic Table, especially palladium, is preferably at least 0.01% by weight, more preferably at least 0.1% by weight, in particular at least 0.15% by weight. This content is preferably at most 5% by weight, more preferably at most 1% by weight, in particular at most 0.6% by weight. Although lower and higher contents are possible, they are normally economically unsatisfactory owing to excessively low activity or excessively high raw material costs. In a particularly preferred embodiment, only one hydrogenating metal, especially palladium, is used.

The ratio of the amounts of hydrogenation metal of group VIII of the Periodic Table of the Elements and additives or dopants is a parameter to be optimized in the individual case. Preferably, the atomic ratio of metal of group VIII of the Periodic Table of the Elements, more preferably palladium, to the promoter, more preferably silver, is preferably 0.1-10, more preferably 2-7, in particular 2.5-6.

The oxidic support of the catalyst used in accordance with the invention is preferably alumina, more preferably in a mixture of δ-, θ- and α-alumina. In addition to unavoidable impurities, the support may also comprise other additives to a certain extent. For example, other inorganic oxides such as oxides of metals of group IA, IIIB, IVB, IIIA and IVA of the Periodic Table of the Elements may be present, especially silicon dioxide, titanium dioxide, zirconium dioxide, zinc oxide, magnesium oxide, sodium oxide and/or calcium oxide. The maximum content in the support of such oxides other than alumina is dependent upon the oxide actually present, but can be determined in the individual case with reference to the X-ray diffractogram of the hydrogenation catalyst, since a change in the structure is accompanied by a significant change in the X-ray diffractogram. In general, the content of such oxides other than alumina is below 50% by weight, preferably below 30% by weight, more preferably below 10% by weight. The purity of the alumina is preferably higher than 99%.

To prepare the support, a suitable aluminum-containing raw material, preferably boehmite, is peptized with a peptizing agent such as water, dilute acid or dilute base. The acid used is, for example, a mineral acid, for instance nitric acid, or an organic acid, for instance formic acid. The base used is preferably an inorganic base, for instance ammonia. The acid or base is generally dissolved in water. The peptizing agent used is preferably water or dilute aqueous nitric acid. The concentration of the nonaqueous fraction in the peptizing agent is generally 0-10% by weight, preferably 0-7% by weight, more preferably 0-5% by weight. After the peptization, the support is shaped, dried and calcined.

Boehmite (γ-AlO(OH)) is a widespread commercial product, but can also be prepared in a known manner immediately before the actual support preparation by precipitation from a solution of an aluminum salt, for example aluminum nitrate, with a base, removal, washing, drying and calcining of the precipitated solid. Advantageously, boehmite is used in the form of a powder. A suitable commercial boehmite powder is, for example, Versal® 250, which is available from UOP. The boehmite is treated with the peptizing agent by moistening it with the peptizing agent and mixing it intensively, for example in a kneader, mixer or edge-runner mill. The peptization is continued until the material is readily shapeable. Subsequently, the material is shaped to the desired shaped support bodies by customary methods, for example by strand pressing, extrusion, tableting or agglomeration. Any known method is suitable for the shaping. If required or advantageous, customary additives may be used. Examples of such additives are extruding or tableting assistants such as polyglycols or graphite.

It is also possible to add additives which, in a known manner, influence the pore structure of the support after calcination as burnout substances to the support raw material before the shaping, for example polymers, fibrous substances, natural burnout substances such as nutshell meals, or other customary additives. Preference is given to using boehmite in a particle size distribution and to the addition of burnout substances, which leads to a pore radius distribution of the finished support at which 50-90% by volume of the total pore volume is present in the form of pores having a mean diameter in the range of 0.01-0.1 µm and 10-50% by volume of the total pore volume is present in the form of pores having a mean diameter in the range of 0.1-1 µm. The measures necessary for this purpose are known per se to those skilled in the art.

After the shaping, the shaped bodies are dried in a customary manner generally at a temperature above 60° C., preferably above 80° C., more preferably above 100° C., especially at a temperature in the range of 120-300° C. The drying is continued until water present in shaped bodies has escaped essentially fully from the shaped bodies, which is generally the case after a few hours. Typical drying times are in the range from 1 to 30 hours and are dependent upon the drying temperature set, a higher temperature shortening the drying time. The drying can be accelerated further by employing a reduced pressure.

After the drying, the shaped bodies are converted to the finished support by calcination. The calcination temperature is generally in the range of 900-1150° C., preferably in the range of 1000-1120° C., more preferably in the range of 1050-1100° C. The calcination time is generally between 0.5 and 5 hours, preferably between 1 and 4 hours, more preferably between 1.5 and 3 hours. The calcination is effected in a customary oven, for example in a rotary oven, in a tunnel oven, in a belt calciner or in a chamber oven. The calcination can directly follow the drying without intermediate cooling of the shaped bodies.

The catalysts usable in accordance with the invention and obtained in this way have a specific surface area (BET, Brunauer-Emmet-Teller, determined to DIN 66131 by nitrogen adsorption at 77 K) of 20-250 m$^2$/g, preferably 50-150 m$^2$/g, in particular 60-90 m$^2$/g. The surface area can be varied by known methods, especially use of finely divided or coarse starting materials, calcination time and calcination temperature. Like the BET surface area, the pore volume can also be varied in a known manner, it is generally, determined by means of mercury porosimetry, in a range of 0.3-1.0 ml/g, preferably in a range of 0.4-0.9 ml/g, more preferably 0.5-0.8 ml/g.

After the calcination, the active composition and, if appropriate, further additives are deposited on the support thus produced.

The support of the inventive catalyst is preferably characterized by the following X-ray diffractogram:

| Interplanar spacing Angström [Å] | Angle 2-Theta [°] | Relative Intensity [%] |
|---|---|---|
| d = 4.552 | 19.483 | 5-15 |
| d = 2.857 | 31.278 | 35-50 |
| d = 2.730 | 32.775 | 65-80 |
| d = 2.449 | 36.671 | 45-55 |
| d = 2.317 | 38.842 | 35-45 |
| d = 2.260 | 39.861 | 5-45 |
| d = 2.022 | 44.790 | 45-65 |
| d = 1.910 | 47.570 | 30-40 |
| d = 1.798 | 50.720 | 10-25 |
| d = 1.543 | 59.915 | 25-35 |
| d = 1.511 | 61.307 | 0-35 |
| d = 1.489 | 62.289 | 20-30 |
| d = 1.455 | 63.926 | 25-35 |
| d = 1.387 | 67.446 | 100 |

This X-ray diffractogram is determined as described in EP 0 992 284 A2 on page 9 lines 6 to 9.

X-ray diffractograms are characteristic of the specific structure of the material analyzed. The structure of the inventive catalyst is defined adequately by occurrence of the above-mentioned reflections. In addition to the above-specified characterizing reflections, it is possible for one or more reflections in any intensity to occur in the X-ray diffractogram for the interplanar spacings 3.48; 2.55, 2.38; 2.09; 1.78; 1.74; 1.62; 1.60; 1.57; 1.42; 1.40 and/or 1.37, all in the unit [Å].

In addition, any further reflections may also occur in the X-ray diffractogram of the catalyst used in accordance with the invention.

The active composition and, if appropriate, further additives may be deposited onto the support thus obtained for the catalyst used in accordance with the invention.

The metals, additives and/or dopants (=promoters) to be deposited onto the support can be applied to the support by any known process, for example by coating from the gas phase (chemical or physical vapor deposition) or impregnation of the support material in a solution which comprises the substances and/or compounds to be deposited.

The preferred method is impregnation with a solution of the substances and/or compounds to be deposited, which are converted to the substances to be deposited in the course of the further catalyst preparation. The substances to be deposited may be deposited individually and/or in portions in a plurality of process steps, or together and fully in one process step. Preference is given to combined deposition in one impregnation step. After the impregnation or after the individual impregnation stages, the supported catalyst is dried and converted by calcining and, if appropriate, other known aftertreatment methods, for example activation and subsequent surface passivation, to the ready-to-use catalyst.

Impregnation processes for depositing active components, additives and/or dopants on a support are known. In general, the support is impregnated with a solution of salts of the components to be deposited, the volume of the solution being such that the solution is absorbed virtually fully by the pore volume of the support ("incipient wetness" method). The concentration of the salts in the solution is such that, after impregnation and conversion of the supported catalyst to the finished catalyst, the components to be deposited are present on the catalyst in the desired concentration. The salts are selected such that they do not leave behind any residues which are troublesome in the catalyst preparation or its later use. Usually, nitrates or ammonium salts are used.

In principle, all impregnation processes known to those skilled in the art are suitable for the preparation of the catalyst used in accordance with the invention.

However, the catalyst used in accordance with the invention is prepared preferably by one-stage impregnation of the support by the incipient wetness method with a nitric acid solution of the nitrates of the metals to be deposited.

In a particularly preferred embodiment, an impregnation solution which comprises palladium nitrate and palladium nitrite together is used.

Additionally present in the impregnation solution is preferably also the metal of group IB of the Periodic Table of the Elements, preferably silver nitrate.

In general, the pH of the impregnation solution is at most 5, preferably at most 2, more preferably at most 1, in particular at most 0.5. The lower limit of the pH is generally 0.2, preferably 0.3, more preferably 0.5. A preferred pH range is, for example, from 0.2 to 2, in particular from 0.3 to 0.5.

After the impregnation, the impregnated support is typically dried, generally at a temperature above 60° C., preferably above 80° C., more preferably above 100° C., in particular at a temperature in the range of 120-300° C. The drying is continued until water present in the impregnated catalyst has escaped essentially fully, which is generally the case after a few hours. Typical drying times are in the range of 1-30 hours and are dependent upon the drying temperature set, a higher drying temperature shortening the drying time. The drying can be accelerated further by employing a reduced pressure.

In a particularly preferred embodiment for the preparation of the catalyst used in accordance with the invention, the impregnated catalyst is dried with simultaneous movement of the impregnated support material, for example in a rotary tube oven.

In a particular embodiment, the air stream used for drying is conducted in countercurrent through the rotary tube.

After the drying, the catalyst is prepared in a customary manner by calcining. This calcination serves essentially to convert the impregnated salts to the components to be deposited or precursors of such components, and differs in this respect from the calcination described above, which serves for the preparation of the support material and of the support structure. In the case of the impregnation of metal nitrates, this calcination essentially decomposes the nitrates to metals and/or metal oxides, which remain in the catalyst, and to nitrous gases, which escape.

The calcination temperature is generally 200-900° C., preferably 280-800° C., more preferably 300-700° C. The calcination time is generally between 0.5 and 20 hours, preferably between 0.5 and 10 hours, more preferably between 0.5 and 5 hours. The calcination is effected in a customary oven, for example in a rotary tube oven, in a belt calciner or in a chamber oven. The calcination can follow the drying directly without intermediate cooling of the supported and dried catalyst.

In a particularly preferred embodiment, the drying and the calcination of the catalyst are combined in a rotary tube oven.

In order to determine the concentrations of metal of group VIII, for example palladium, and promoter, for example silver, via the extrudate cross section, methods known to those skilled in the art can be used. One of these methods is electron microscopy, for example Scanning Electron Microscopy (SEM) or Electron Probe Microanalysis (EPMA). Another technique is to cut through the catalyst extrudate, to treat it with a reducing agent (e.g. hydrogen), in order to bring about a color change in order thus to determine the distribution of the metals.

After the calcination, the catalyst is in principle ready for use. If required or desired, it is activated by prereduction in a known manner and, if appropriate, also surface-passivated again before it is installed into the reactor for the aminating hydrogenation.

In general, the catalyst is, however, usually not reduced until within the reactor for the aminating hydrogenation. This is done in a manner known to the person skilled in the art by initial inertization with nitrogen or another inert gas. The reduction is performed with a hydrogenous gas as a pure gas phase or with inert circulation. The temperature at which this prereduction is performed is generally 5-200° C., preferably 20-150° C.

It is also possible to regenerate the catalyst used in accordance with the invention outside or inside the reactor for the aminating hydrogenation at temperatures of from 15 to 500° C.

The above-described catalysts are used in accordance with the invention in a process for preparing an amine by reacting an aldehyde and/or ketone with hydrogen and a nitrogen compound selected from the group of primary and secondary amines (aminating hydrogenation).

As a result of the use of the catalysts, these aldehydes and ketones can be converted to the corresponding secondary and tertiary amines with high selectivity and high yield.

The carbonyl compound is aminated preferably in the liquid phase.

In the case of amination in the liquid phase, one adiabatic reactor with or without recycling may suffice.

The catalyst is arranged in the reactor for the aminating hydrogenation (e.g. tubular reactor) preferably as a fixed bed.

In one embodiment of the invention, the reaction is performed in the liquid phase or in a mixed liquid/gas phase with at least 50% by weight of the reaction mixture in the liquid phase.

In one embodiment of the invention, the amination can be performed in trickle mode or in liquid-phase mode.

In the liquid-phase mode, the hydrogenation hydrogen added may be present in dissolved form in the liquid phase.

The entrance temperature of the reactant mixture in the amination is, in one embodiment of the invention, from −10 to 250° C., preferably from 0 to 180° C., in particular from 50 to 150° C.

In order to ensure the formation of the liquid phase, suitable temperature and pressure parameters have to be selected within the abovementioned ranges, which is dependent upon the particular substance mixture used.

The nitrogen compound is used preferably in from 0.90 to 100 times the molar amount, especially in from 1.0 to 10 times the molar amount, based in each case on the aldehyde and/or ketone used.

The process according to the invention is preferably performed at a catalyst hourly space velocity—measured as the mass of aldehyde or ketone in the feed based on the catalyst volume and the time—in the range from 0.01 to 2.00 kg (carbonyl compound)/liter (catalyst)/h, preferably from 0.10 to 1.50 kg/liter/h, more preferably from 0.20 to 1.20 kg/liter/h, especially preferably from 0.22 to 1.00 kg/liter/h.

The process according to the invention is performed preferably at an absolute pressure in the range from 1 to 325 bar, preferably from 10 to 250 bar, more preferably from 100 to 200 bar, especially preferably from 85 to 150 bar, for example from 90 to 135 bar.

The process according to the invention for aldehyde and/or ketone amination is performed preferably at a temperature in the range from 50 to 280° C., preferably from 80 to 250° C., more preferably from 120 to 210° C.

Preference is given to operating with an offgas rate of from 5 to 800 standard cubic meters/h, especially from 20 to 300 standard cubic meters/h.

The use of higher temperatures, higher overall pressures and higher loads is possible. The pressure in the reactor, which arises from the sum of the partial pressures of the aminating agent, of the aldehyde and/or ketone component and of the reaction products formed at the temperatures specified, is appropriately increased by injecting hydrogen to the desired reaction pressure.

The water of reaction formed in the course of the reaction generally does not have a disruptive effect on the conversion, the reaction rate, the selectivity and the catalyst lifetime and is therefore appropriately not removed therefrom until the workup of the reaction product, for example by distillation.

Once the reaction effluent has appropriately been decompressed, the excess hydrogen and any excess aminating agent present are removed therefrom, and the resulting crude reaction product is purified, for example by a fractional rectification. Suitable workup processes are described, for example, in EP-A-1 312 600 and EP-A-1 312 599 (both BASF AG).

Unconverted reactants and any suitable by-products which occur can be recycled back into the synthesis. Unconverted reactants can be flowed over the catalyst bed again in the cycle gas stream in discontinuous or continuous mode after the products have been condensed in the separator.

It is possible by the process according to the invention to prepare, for example, amines of the formula I

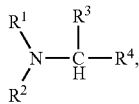
(I)

in which

R$^1$, R$^2$ are each hydrogen (H), alkyl such as C$_{1-20}$-alkyl, cycloalkyl such as C$_{3-12}$-cycloalkyl, alkoxyalkyl such as C$_{2-30}$-alkoxyalkyl, dialkylaminoalkyl such as C$_{3-30}$-dialkylaminoalkyl, aryl, aralkyl such as C$_{7-20}$-aralkyl and alkylaryl such as C$_{7-20}$-alkylaryl, or together are —(CH$_2$)$_j$—X—(CH$_2$)$_k$—, R$^3$, R$^4$ are each hydrogen (H), alkyl such as C$_{1-2}$-alkyl, cycloalkyl such as C$_{3-12}$-cycloalkyl, hydroxyalkyl such as C$_{1-20}$-hydroxyalkyl, aminoalkyl such as C$_{1-20}$-aminoalkyl, hydroxyalkylaminoalkyl such as C$_{2-20}$-hydroxyalkylaminoalkyl, alkoxyalkyl such as C$_{2-30}$-alkoxyalkyl, dialkylaminoalkyl such as C$_{3-30}$-dialkylaminoalkyl, alkylaminoalkyl such as C$_{2-30}$-alkylaminoalkyl, R$^5$—(OCR$^6$R$^7$CR$^8$R$^9$)$_n$—(OCR$^6$R$^7$), aryl, heteroaryl, aralkyl such as C$_{7-20}$-aralkyl, heteroarylalkyl such as C$_{4-20}$-heteroarylalkyl, alkylaryl such as C$_{7-20}$-alkylaryl, alkylheteroaryl such as C$_{4-20}$-alkylheteroaryl, and Y—(CH$_2$)$_m$—NR$^5$—(CH$_2$)$_q$ or, together, —(CH$_2$)$_l$—X—(CH$_2$)$_m$— or R$^2$ and R$^4$ together are —(CH$_2$)$_l$—X—(CH$_2$)$_m$—, R$^5$, R$^{10}$ are each hydrogen (H), alkyl such as C$_{1-4}$-alkyl, alkylphenyl such as C$_{7-40}$-alkylphenyl, R$^6$, R$^7$, R$^8$, R$^9$ are each hydrogen (H), methyl or ethyl, x is CH$_2$, CHR$^5$, oxygen (O), sulfur (S) or NR$^5$, Y is N(R$^{10}$)$_2$, hydroxyl, C$_{2-20}$-alkylaminoalkyl or C$_{3-20}$-dialkylaminoalkyl, n is an integer from 1 to 30 and j, k, l, m, q are each integers from 1 to 4.

The process according to the invention therefore preferably finds use for preparing an amine I by reacting an aldehyde and/or a ketone of the formula VI or VII

(VI)

(VII)

with a nitrogen compound of the formula III

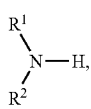
(III)

where R$^1$, R$^2$, R$^3$ and R$^4$ are each as defined above.

As is evident from the definitions of the R$^2$ and R$^4$ radicals, the reaction can also be effected intramolecularly in an appropriate amino ketone or amino aldehyde.

To prepare the amine 1, in a purely formal sense, a hydrogen atom of the nitrogen compound III is accordingly replaced by the R$^4$(R$^3$)CH— radical with release of one molar equivalent of water.

The substituents R$^1$ to R$^{10}$, the variables X, Y, and the indices j, k, l, m, n and q in the compounds I, III, VI and VII are each independently defined as follows:

R$^1$, R$^2$, R$^3$, R$^4$, R$^5$, R$^6$, R$^7$, R$^8$, R$^9$, R$^{10}$:

hydrogen (H), (R$^1$ and R$^2$ are not both simultaneously H),

R$^3$, R$^4$:

alkyl such as C$_{1-20}$-alkyl, preferably C$_{1-14}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, hydroxyalkyl such as C$_{1-20}$-hydroxyalkyl, preferably C$_{1-8}$-hydroxyalkyl, more preferably C$_{1-4}$-hydroxyalkyl, such as hydroxymethyl, 1-hydroxyethyl, 2-Hydroxyethyl, 1-hydroxy-n-propyl, 2-hydroxy-n-propyl, 3-hydroxy-n-propyl and 1-(hydroxymethyl)ethyl, aminoalkyl such as C$_{1-20}$-aminoalkyl, preferably C$_{1-8}$-aminoalkyl, such as aminomethyl, 2-aminoethyl, 2-amino-1,1-dimethylethyl, 2-amino-n-propyl, 3-amino-n-propyl, 4-amino-n-butyl, 5-amino-n-pentyl, N-(2-aminoethyl)-2-aminoethyl and N-(2-aminoethyl)aminomethyl, hydroxyalkylaminoalkyl such as C$_{2-20}$-hydroxyalkylaminoalkyl, preferably C$_{3-8}$-hydroxyalkylaminoalkyl, such as (2-hydroxyethylamino) methyl, 2-(2-hydroxyethylamino) ethyl and 3-(2-hydroxyethylamino)propyl, R$^5$—(OCR$^6$R$^7$CR$^8$R$^9$)$_n$—(OCR$^6$R$^7$), preferably R$^5$—(OCHR$^7$CHR$^9$)$_n$—(OCR$^6$R$^7$), more preferably R$^5$—(OCH$_2$CHR$^9$)$_n$—(OCR$^6$R$^7$), alkylaminoalkyl such as C$_{2-30}$-alkylaminoalkyl, preferably C$_{2-20}$-alkylaminoalkyl, more preferably C$_{2-8}$-alkylaminoalkyl, such as methylaminomethyl, 2-methylaminoethyl, ethylaminomethyl, 2-ethylaminoethyl and 2-(isopropylamino)ethyl, (R$^5$)HN—(CH$_2$)$_q$, Y—(CH$_2$)$_m$—NR$^5$—(CH$_2$)$_q$, heteroarylalkyl such as C$_{4-20}$-heteroarylalkyl, such as pyrid-2-ylmethyl, furan-2-ylmethyl, pyrrol-3-ylmethyl and imidazol-2-ylmethyl, alkylheteroaryl such as C$_{4-20}$-alkylheteroaryl, such as 2-methyl-3-pyridinyl, 4,5-dimethylimidazol-2-yl, 3-methyl-2-furanyl and 5-methyl-2-pyrazinyl, heteroaryl such as 2-pyridinyl, 3-pyridinyl, 4-pyridinyl, pyrazinyl, pyrrol-3-yl, imidazol-2-yl, 2-furanyl and 3-furanyl,

R$^1$, R$^2$, R$^3$, R$^4$:

cycloalkyl such as C$_{3-12}$-cycloalkyl, preferably C$_{3-8}$-cycloalkyl, such as cyclopropyl, cyclobutyl, cyclopentyl, cyclohexyl, cycloheptyl and cyclooctyl, more preferably cyclopentyl and cyclohexyl, alkoxyalkyl such as C$_{2-30}$-alkoxyalkyl, preferably C$_{2-20}$-alkoxyalkyl, more preferably C$_{2-8}$-alkoxyalkyl, such as methoxymethyl, ethoxymethyl, n-propoxymethyl, isopropoxymethyl, n-butoxymethyl, isobutoxymethyl, sec-butoxymethyl, tertbutoxymethyl, 1-methoxyethyl and 2-methoxyethyl, more preferably C$_{2-4}$-alkoxyalkyl, dialkylaminoalkyl such as C$_{3-30}$-dialkylaminoalkyl, preferably C$_{3-20}$-dialkylaminoalkyl, more preferably C$_{3-10}$-dialkylaminoalkyl, such as N,N-dimethylaminomethyl, (N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino)ethyl and 2-(N,N-diisopropylamino)ethyl, 3-(N,N-dimethylamino)propyl, $(R^5)_2N—(CH_2)_q$, aryl such as phenyl, 1-naphthyl, 2-naphthyl, 1-anthryl, 2-anthryl and 9-anthryl, preferably phenyl, 1-naphthyl and 2-naphthyl, more preferably phenyl, alkylaryl such as $C_{7-20}$-alkylaryl, preferably $C_{7-12}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, aralkyl such as $C_{7-20}$-aralkyl, preferably $C_{7-12}$-phenylalkyl, such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, more preferably benzyl, 1-phenethyl and 2-phenethyl, $R^3$ and $R^4$ or $R^2$ and $R^4$ together are a $—(CH_2)_j—X—(CH_2)_m—$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR_5—(CH_2)_3—$, $R^1$, $R^2$:

alkyl such as $C_{1-20}$-alkyl, preferably $C_{1-8}$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, more preferably $C_{1-4}$-alkyl, or $R^1$ and $R^2$ together are a $—(CH_2)_j—X—(CH_2)_k—$ group such as $—(CH_2)_3—$, $—(CH_2)_4—$, $—(CH_2)_5—$, $—(CH_2)_6—$, $—(CH_2)_7—$, $—(CH_2)—O—(CH_2)_2—$, $—(CH_2)—NR^5—(CH_2)_2—$, $—(CH_2)—CHR^5—(CH_2)_2—$, $—(CH_2)_2—O—(CH_2)_2—$, $—(CH_2)_2—NR^5—(CH_2)_2—$, $—(CH_2)_2—CHR^5—(CH_2)_2—$, $—CH_2—O—(CH_2)_3—$, $—CH_2—NR^5—(CH_2)_3—$, $—CH_2—CHR^5—(CH_2)_3—$, $R^5$, $R^{10}$:

alkyl, preferably $C_{1-4}$-alkyl, such as methyl, ethyl, n-propyl, isopropyl, n-butyl, isobutyl, sec-butyl and tert-butyl, preferably methyl and ethyl, more preferably methyl, alkylphenyl, preferably $C_{7-40}$-alkylphenyl, such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, in particular $C_{7-20}$-alkylphenyl, $R^6$, $R^7$, $R^8$, $R^9$:

methyl or ethyl, preferably methyl,

X:

$CH_2$, $CHR^5$, oxygen (O), sulfur (S) or $NR^5$, preferably $CH_2$ and O,

Y:

$N(R^{10})_2$, preferably $NH_2$ and $N(CH_3)_2$, hydroxyl (OH), $C_{2-20}$-alkylaminoalkyl, preferably $C_{2-16}$-alkylaminoalkyl, such as methylaminomethyl, 2-methylaminoethyl, ethylaminomethyl, 2-ethylaminoethyl and 2-(isopropylamino)ethyl, $C_{3-20}$-dialkylaminoalkyl, preferably $C_{3-16}$-dialkylaminoalkyl, such as dimethylaminomethyl, 2-dimethylaminoethyl, 2-diethylaminoethyl, 2-(di-n-propylamino)ethyl and 2-(diisopropylamino)ethyl, j, l:

an integer from 1 to 4 (1, 2, 3 or 4), preferably 2 and 3, more preferably 2, k, m, q:

an integer from 1 to 4 (1, 2, 3 or 4), preferably 2, 3 and 4, more preferably 2 and 3, n:

an integer from 1 to 30, preferably an integer from 1 to 8 (1, 2, 3, 4, 5, 6, 7 or 8), more preferably an integer from 1 to 6.

Suitable ketones usable in accordance with the invention are, under the abovementioned prerequisites, virtually all aliphatic and aromatic ketones. The aliphatic ketones may be straight-chain, branched or cyclic; the ketones may comprise heteroatoms. The ketones may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds, When polyfunctional ketones are to be aminated, it is possible via the control of the reaction conditions to obtain amino ketones, amino alcohols, cyclic amines or polyaminated products.

Preference is given, for example, to aminatingly hydrogenating the following ketones: acetone, ethyl methyl ketone, methyl vinyl ketone, isobutyl methyl ketone, butanone, 3-methylbutan-2-one, diethyl ketone, tetralone, acetophenone, propiophenone, p-methylacetophenone, p-methoxyacetophenone, m-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Suitable aldehydes usable in accordance with the invention are, under the abovementioned prerequisites, virtually all aliphatic and aromatic aldehydes. The aliphatic aldehydes may be straight-chain, branched or cyclic; the aldehydes may comprise heteroatoms. The aldehydes may further bear substituents or comprise functional groups which behave inertly under the conditions of the hydrogenating amination, for example alkoxy, alkenyloxy, alkylamino or dialkylamino groups, or else, if appropriate, are hydrogenated under the conditions of the hydrogenating amination, for example C—C double or triple bonds. When polyfunctional aldehydes or keto aldehydes are to be aminated, it is possible via the control of the reaction conditions to obtain amino alcohols, cyclic amines or polyaminated products.

Preference is given, for example, to aminatingly hydrogenating the following aldehydes:

formaldehyde, acetaldehyde, propionaldehyde, n-butyraldehyde, isobutyraldehyde, pivalaldehyde, n-pentanal, n-hexanal, 2-ethylhexanal, 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronelial, lysmeral, acrolein, methacrolein, ethylacrolein, citral, crotonaldehyde, 3-methoxypropionaldehyde, 3-aminopropionaldehyde, hydroxypivalaldehyde, dimethylolpropionaldehyde, dimethylolbutyraldehyde, furfural, glyoxal, glutaraldehyde and hydroformylated oligomers and polymers, for example hydroformylated polyisobutene (polyisobutenealdehyde) or hydroformylated oligomer obtained by metathesis of 1-pentene and cyclopentene.

The aminating agents used in the hydrogenating amination of aldehydes and/or ketones in the presence of hydrogen may be primary or secondary, aliphatic or cycloaliphatic or aromatic amines.

From di- or oligoaldehydes or di- or oligoketones or keto aldehydes, it is possible by intramolecular hydrogenating amination to prepare cyclic amines, for example pyrrolidines, piperidines, hexamethyleneimines, piperazines and morpholines.

Preference is given to using the primary or secondary amines as aminating agents to prepare unsymmetrically substituted di- or trialkylamines such as ethyldiisopropylamine and ethyldicyclohexylamine.

For example, the following mono- and dialkylamines are used as aminating agents: methylamine, dimethylamine, ethylamine, diethylamine, n-propylamine, di-n-propylamine, isopropylamine, diisopropylamine, dimethylmorpholine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

Amines prepared with particular preference by the process according to the invention are, for example, N,N-di($C_{1-4}$-alkyl)cyclohexylamine (from cyclohexanone and di($C_{1-4}$-alkyl)amine), n-propylamines (such as dimethylpropylamine) (from propionaldehyde and DMA), N,N-dimethyl-N-isopropylamine (from acetone and DMA), N,N-dimethyl-N-butylamines (from butanal, i-butanal or butanone and DMA), N-ethyl-N,N-diisopropylamine (from acetaldehyde and N,N-diisopropylamine), cis-4-[3-(4-tert-butylphenyl)-2-methylpropyl]-2,6-dimethyl morpholine (from lysmeral and cis-2,6-dimethylmorpholine) and tris(2-ethylhexyl)amine (from 2-ethylhexanal and di(2-ethylhexyl)amine).

EXAMPLES

Preparation of an Inventive Catalyst $Al_2O_3$ extrudates (diameter 2.8 mm) having a surface area of 60-90 m²/g were treated with an impregnation solution comprising palladium nitrate, palladium nitrite and silver nitrate which has been acidified to a pH in the range from 0.2 to 2 with concentrated (69%) nitric acid. The content of the added nitric acid in the finished impregnation solution was 1.8% by weight. The moist extrudates were dried at 200° C. and calcined at 600° C. A catalyst was obtained which comprised 0.3% by weight of palladium and 0.1% by weight of silver, the weight ratio of palladium to silver being 3. The distribution of the elements over the extrudate cross section, measured by the Electron Probe Microanalysis (EPMA) technique, was as follows:

at least 80% of the palladium (Pd) was present in a layer between the surface of the catalyst and a penetration depth which corresponded to not more than 80% of the radius of the catalyst, calculated from the surface of the catalyst, and the promoter (Ag) was present over the entire cross section of the catalyst.

The following experiments were effected in an electrically heated 1 liter tubular reactor in a continuous reaction. The reaction effluents were analyzed by means of gas chromatography. The analysis programs used were: a) DB1 column, length 60 m; internal diameter 0.32 mm; helium carrier gas; temperature program: 80° C. then at 8° C./minutes to 280° C., finally 15 minutes isothermal at 280° C., and b) Rtx-5-amine column, length 30 m; internal diameter 0.32 mm; helium carrier gas; temperature program: 70° C. for 5 minutes, then at 5° C./minutes to 280° C., finally 10 minutes isothermal at 280° C. The product composition is reported as GC area percent of the crude effluents, calculated without water and without the excess of feedstock amine component.

Example 1

Fenpropimorph

Fenpropimorph (cis-FPM) was prepared by reductive amination from technical-grade lysmeral (lyal) and cis-2,6-dimethylmorpholine (DMM) in the presence of hydrogen and of an inventive fixed bed catalyst. The reaction was performed in the liquid phase (liquid-phase or trickle mode).

The technical-grade lysmeral (approx. 95% pure) and dimethylmorpholine (>97% pure) reactants were metered into the reactor with separate feeds at total pressure of from 50 to 140 bar, and reacted at from 200 to 240° C. in straight pass with liquid recycling. The synthesis was effected with a catalyst hourly space velocity of from 0.25 up to 0.50 kg (lyal)/(liter (cat.)·h) at a molar DMM/lyal ratio of 2.5. The lysmeral and dimethylmorpholine feedstocks were converted virtually quantitatively. The reaction proceeded very selectively, which is why only small amounts of secondary components were present in the reaction effluent. Secondary components of the reaction were lysmerol (lyol) from the unselective hydrogenation of lysmeral (lyol is additionally present in the starting material to an extent of 2%) and the enamines formed from lysmeral and DMM (intermediate in the synthesis of cis-FPM). The experimental results are listed in the following Table 1.

TABLE 1

Synthesis of fenpropimorph (liquid-phase and trickle mode)

| Run time [h] | Temperature [° C.] | Pressure [bar] | Catalyst hourly space velocity [kg/liter/h] | cis-FPM [%] | Lyol [%] | Lyal [%] | Enamines [%] |
|---|---|---|---|---|---|---|---|
| 0-200 | 200 | 90 | 0.31 | 97 | 2 | 0.1 | 0.5 |
| 200-350 | 220 | 90 | 0.31 | 97 | 2 | 0.1 | 0.5 |
| 350-500 | 220 | 140 | 0.31 | 97 | 2 | 0.1 | 0.5 |
| 500-700 | 200 | 140 | 0.31 | 97 | 2 | 0.1 | 1 |
| 700-800 | 200 | 50 | 0.31 | 97 | 2 | 0.2 | 1 |
| 800-1000 | 220 | 50 | 0.31 | 97 | 2 | 0.1 | 0.5 |
| 1000-1200* | 200 | 90 | 0.31 | 91 | 2 | 1 | 6 |
| 1200-1300* | 220 | 90 | 0.31 | 94 | 2 | 0.5 | 3 |
| 1300-1400* | 220 | 140 | 0.31 | 93 | 3 | 0.5 | 3 |

TABLE 1-continued

Synthesis of fenpropimorph (liquid-phase and trickle mode)

| Run time [h] | Temperature [° C.] | Pressure [bar] | Catalyst hourly space velocity [kg/liter/h] | cis-FPM [%] | Lyol [%] | Lyal [%] | Enamines [%] |
|---|---|---|---|---|---|---|---|
| 1400-1500* | 220 | 50 | 0.31 | 93 | 2 | 0.5 | 4 |
| 2200-2300 | 240 | 90 | 0.5 | 96 | 3 | 0.1 | 1 |
| 2300-2400 | 240 | 140 | 0.5 | 96 | 3 | 0.1 | 1 |
| 2400-2500 | 240 | 50 | 0.5 | 97 | 2 | 0.1 | 1 |
| 2500-2600 | 220 | 140 | 0.25 | 96 | 3 | 0.1 | 1 |
| 2800-2900 | 240 | 90 | 0.25 | 96 | 3 | 0.1 | 0.5 |
| 2900-3000 | 240 | 50 | 0.25 | 96 | 3 | 0.1 | 0.5 |
| 3000-3100 | 220 | 90 | 0.25 | 96 | 3 | 0.1 | 1 |

*In trickle mode, remaining entries: liquid-phase mode

Comparative Example 1

Fenpropimorph

Fenpropimorph was prepared by reductive amination from technical-grade lysmeral and cis-2,6-dimethylmorpholine in the same reactor as in Example 1. The catalyst used was a silver- and palladium-containing fixed bed catalyst which had silicon dioxide as a support and did not have a coating structure of the catalytically active metals. The experiments were otherwise performed under comparable reaction conditions. Owing to a comparatively low catalyst activity, increased enamine contents in the reaction effluent were often determined. The reaction proceeded less selectively; lysmerol was formed as a secondary component to an increased extent. The experimental results are compiled in the following Table 2.

TABLE 2

Synthesis of fenpropimorph (liquid-phase mode)

| Run time [h] | Temperature [° C.] | Pressure [bar] | Catalyst hourly space velocity [kg/liter/h] | cis-FPM [%] | Lyol [%] | Lyal [%] | Enamines [%] |
|---|---|---|---|---|---|---|---|
| 150-250 | 190 | 50 | 0.31 | 89 | 3 | 1 | 7 |
| 250-350 | 170 | 50 | 0.31 | 82 | 3 | 2 | 13 |
| 500-580 | 170 | 140 | 0.31 | 87 | 4 | 1 | 8 |
| 580-620 | 190 | 140 | 0.31 | 91 | 4 | 1 | 4 |
| 620-660 | 240 | 140 | 0.31 | 95 | 4 | 0.1 | 0.5 |

Example 2

Dimethylcyclohexylamine

N,N-Dimethylcyclohexylamine (DMCHA) is prepared by reductive amination from cyclohexanone (anon) and dimethylamine (DMA) in the presence of hydrogen and of an inventive fixed bed catalyst. The reaction is performed in the liquid phase in trickle or liquid-phase mode.

The cyclohexanone (99.5% pure) and dimethylamine (>99% pure) reactants were metered into the reactor at total pressure from 90 to 130 bar. The separate feeds were mixed upstream of the reactor. The reaction was effected at from 160 to 220° C. in straight pass without liquid recycling. The synthesis was effected with a catalyst hourly space velocity of from 0.15 up to 0.80 kg (anon)/(liter(cat.)·h) at a molar DMA/anon ratio of from 2.3 to 3.0. The cyclohexanone and dimethylamine feedstocks were converted virtually quantitatively. The reaction proceeded very selectively, which is why only small amounts of alcohol (cyclohexanol) were present in the reaction effluent. Another side reaction was "scrambling", the formation of monomethylcyclohexylamine (MMCHA) by methyl group migration in DMCHA and DMA. The experimental results are listed in the following Table 3.

TABLE 3

Synthesis of DMCHA (liquid-phase mode)

| Run time [h] | Temperature [° C.] | Pressure [bar] | Molar ratio of amine [ketone] | Catalyst hourly space velocity [kg/L/h] | DMCHA [%] | MMCHA [%] | Cyclohexanol [%] | Cyclohexanone [%] |
|---|---|---|---|---|---|---|---|---|
| 100-250 | 160 | 130 | 2.3 | 0.15 | 97 | 0.1 | 1 | 2 |
| 250-350 | 190 | 130 | 2.3 | 0.3 | 98 | 0.5 | 1 | 0.5 |
| 350-400 | 220 | 130 | 2.3 | 0.45 | 96 | 3 | 1 | 0.1 |
| 400-700 | 195 | 90 | 2.3 | 0.45 | 98 | 1 | 0.5 | 0.5 |
| 700-800 | 220 | 130 | 2.3 | 0.8 | 96 | 3 | 0.5 | 0.5 |
| 800-1000 | 205 | 130 | 3.0 | 0.6 | 97 | 2 | 0.5 | 0.1 |

Comparative Example 2

Dimethylcyclohexylamine

N,N-Dimethylcyclohexylamine was prepared by reductive amination of cyclohexanone and dimethylamine in the same reactor as in Example 2. The catalyst used was a silver- and palladium-containing fixed bed catalyst which had silicon dioxide as a support and did not have a coating structure of the catalytically active metals. The experiments were otherwise performed under comparable reaction conditions. The reaction proceeded less selectively; cyclohexanol was formed as a secondary component by hydrogenation of cyclohexanone to an increased extent. The experimental results are compiled in Table 4.

TABLE 4

Synthesis of DMCHA (liquid-phase mode)

| Run time [h] | Temperature [° C.] | Pressure [bar] | Molar ratio of amine [ketone] | Catalyst hourly space velocity [kg/liter/h] | DMCHA [%] | MMCHA [%] | Cyclohexanol [%] | Cyclohexanone [%] |
|---|---|---|---|---|---|---|---|---|
| 0-100 | 160 | 130 | 2.2 | 0.2 | 94 | 0.2 | 5 | 0.5 |
| 100-150 | 160 | 130 | 2.2 | 0.3 | 96 | 0.1 | 3 | 1 |
| 150-250 | 160 | 100 | 2.2 | 0.3 | 97 | 0.1 | 2 | 1 |
| 250-300 | 160 | 85 | 2.2 | 0.3 | 96 | 0.1 | 2 | 1.5 |
| 300-350 | 170 | 85 | 2.2 | 0.3 | 96 | 0.1 | 2 | 1.5 |
| 350-400 | 180 | 85 | 2.2 | 0.3 | 96 | 0.5 | 2 | 1 |

The invention claimed is:

1. A process for preparing an amine comprising reacting an aldehyde and/or a ketone with hydrogen and a nitrogen compound selected from the group consisting of primary amines and secondary amines in the presence of a heterogeneous catalyst, wherein said heterogeneous catalyst is a coated catalyst comprising (1) at least one metal of group VIII of the Periodic Table of the Elements as a hydrogenating metal and (2) a promoter on an oxidic support, wherein at least 80% of said at least one metal of group VIII of the Periodic Table of the Elements is present in a layer between the surface of the catalyst and a penetration depth of not more than 80% of the radius of said heterogeneous catalyst, as calculated from the surface of said heterogeneous catalyst, and wherein said promoter is substantially homogeneously distributed over the entire cross section of said heterogeneous catalyst.

2. The process of claim 1, wherein said heterogeneous catalyst has a diameter in the range of from 2.5 to 10 mm and at least 80% of said at least one metal of group VIII of the Periodic Table of the Elements is present in a layer between the surface of the catalyst and a penetration depth of not more than 1000 μm, as calculated from the surface of said heterogeneous catalyst.

3. The process of claim 1, wherein said oxidic support is alumina.

4. The process of claim 1, wherein said oxidic support is a mixture of δ-, θ-, and α-alumina.

5. The process of claim 1, wherein said at least one metal of group VIII of the Periodic Table of the Elements is palladium.

6. The process of claim 1, wherein said at least one metal of group VIII of the Periodic Table is present in said heterogenous catalyst in an amount in the range of from 0.05 to 5% by weight, based on the total weight of said heterogenous catalyst.

7. The process of claim 1, wherein said promoter is a metal of group IB of the Periodic Table of the Elements.

8. The process of claim 7, wherein said metal of group IB of the Periodic Table of the Elements is silver.

9. The process of claim 7, wherein the atomic ratio of said at least one metal of group VIII of the Periodic Table of the Elements to said metal of group IB of the Periodic Table of the Elements is in the range of from 0.1 to 10.

10. The process of claim 1, wherein said heterogenous catalyst is prepared by impregnating an oxidic support with a solution comprising nitrate and nitrite salts of metals of group VIII and IB of the Periodic Table of the Elements, acidifying the resulting impregnated oxidic support with nitric acid, drying said impregnated oxidic support, and calcining said impregnated oxidic support.

11. The process of claim 1, wherein said heterogeneous catalyst is arranged as a fixed bed in a reactor.

12. The process of claim 1, wherein said reaction is performed continuously.

13. The process of claim 1, wherein said reaction is performed in the liquid phase.

14. The process of claim 1, wherein said reaction is performed in the liquid phase or in a mixed liquid/gas phase wherein at least 50% by weight of the reaction mixture is in the liquid phase.

15. The process of claim 1, wherein the reaction is performed at a catalyst hourly space velocity, as measured as a mass of aldehyde or ketone in the feed based on the catalyst volume and time, in the range of from 0.01 to 2.00 kg (carbonyl compound)/liter(catalyst)/h.

16. The process of claim 1, wherein said reaction is performed at a temperature in the range of from 50 to 280° C.

17. The process of claim 1, wherein said reaction is performed at an absolute pressure in the range of from 1 to 325 bar.

18. The process of claim 1, wherein said nitrogen compound is used in an amount that is in the range of from 0.90 to 100 times the molar amount of said aldehyde and/or said ketone used.

19. The process of claim 1, wherein cis-4-[3-(4-tert-butylphenyl)-2-methylpropyl]-2,6-dimethylmorpholine is prepared by reacting lysmeral with cis-2,6-dimethylmorpholine.

20. The process of claim 1, wherein N,N-dimethylcyclohexylamine is prepared by reacting cyclohexanone with dimethylamine.

21. The process of claim 1, wherein N,N-dimethyl-N-isopropylamine is prepared by reacting acetone with dimethylamine.

22. The process of claim 1, wherein N-ethyl-N,N-diisopropylamine is prepared by reacting acetaldehyde with N,N-diisopropylamine.

23. The process of claim 1, wherein dicyclohexylamine is prepared by reacting cyclohexanone with cyclohexylamine.

24. The process of claim 1, wherein butylethylamine is prepared by reacting butanal with ethylamine.

25. The process of claim 1, wherein tris(2-ethylhexyl) amine is prepared by reacting ethylhexanal with bis(2-ethylhexyl)amine.

26. The process of claim 1, wherein N-(cyclododecyl)-2,6-dimethylmorpholine is prepared by reacting cyclododecanone with trans-2,6-dimethylmorpholine.

27. The process of claim 1, wherein said heterogenous catalyst has a diameter in the range of from 1.5 to 9 mm.

* * * * *